United States Patent
Krastev

(10) Patent No.: US 9,333,058 B1
(45) Date of Patent: May 10, 2016

(54) VARIABLE GEOMETRY OSTEOTOME FOR RIDGE EXPANSION

(71) Applicant: Pavel Krastev, New Hyde Park, NY (US)

(72) Inventor: Pavel Krastev, New Hyde Park, NY (US)

(*) Notice: Subject to any disclaimer, the term of this patent is extended or adjusted under 35 U.S.C. 154(b) by 162 days.

(21) Appl. No.: 14/036,152

(22) Filed: Sep. 25, 2013

Related U.S. Application Data

(63) Continuation-in-part of application No. 14/033,031, filed on Sep. 20, 2013.

(60) Provisional application No. 61/705,659, filed on Sep. 26, 2012.

(51) Int. Cl.
*A61C 3/02* (2006.01)
*A61C 8/00* (2006.01)

(52) U.S. Cl.
CPC ................. *A61C 8/0092* (2013.01); *A61C 3/02* (2013.01)

(58) Field of Classification Search
CPC .................................... A61C 8/00; A61C 3/02
USPC .............................. 606/80–85, 86 R; 433/144
See application file for complete search history.

(56) References Cited

U.S. PATENT DOCUMENTS

| | | | |
|---|---|---|---|
| 3,924,493 A | 12/1975 | Penner | |
| 4,508,005 A | 4/1985 | Herman | |
| 5,514,113 A | 5/1996 | Anderson | |
| 5,685,716 A | 11/1997 | Linkow | |
| 5,997,298 A * | 12/1999 | Nowak | 433/165 |
| 6,171,312 B1 | 1/2001 | Beaty | |
| 7,125,253 B2 | 10/2006 | Kitamura | |
| 7,241,144 B2 * | 7/2007 | Nilo et al. | 433/174 |
| 7,396,232 B2 | 7/2008 | Fromovich | |
| 7,632,280 B2 | 12/2009 | Hochman | |
| 7,771,199 B2 | 8/2010 | Hochman | |
| 8,075,564 B2 | 12/2011 | Lee | |
| 8,083,747 B2 | 12/2011 | Song | |

(Continued)

FOREIGN PATENT DOCUMENTS

WO    WO2004043303    5/2004

OTHER PUBLICATIONS

Vladimir Koifman, "Fraunhofer Institute and Awaiba Developed 1 mm>3 Camera," Image Sensors World, News and Discussions about Image Sensors, Mar. 11, 2011, http://image-sensors-world.blogspot.com/2011/03/fraunhofer-institute-and-awaiba.html.

(Continued)

*Primary Examiner* — Christopher Beccia
(74) *Attorney, Agent, or Firm* — Thomas A. O'Rourke; Bodner & O'Rourke, LLP

(57) ABSTRACT

A set of Osteotomes used for forming an implant socket during a ridge expansion osteotomy may be specially constructed to reduce crestal alveolar stress and to reduce likelihood of a crestal fracture. Each osteotome includes a conical working tip having a free end and a working base. A first osteotome of the set has a working tip formed with a first diameter, Y, at the free end, and a second diameter, X, at the working base, with the second diameter being larger than the first diameter, X>Y; and wherein for each successive osteotome of the set, the diameter at the free end increases linearly by a constant increment, k, and the diameter at the working base alternately increases by a constant increment, C, as a step function. Other interrelationships between the free end and the working base of the previous and successive osteotomes operate to maintain crestal integrity.

5 Claims, 5 Drawing Sheets

(56) References Cited

U.S. PATENT DOCUMENTS

| | | |
|---|---|---|
| 8,282,640 B2 | 10/2012 | Hung |
| 2007/0042326 A1 | 2/2007 | Cardoso |
| 2008/0275379 A1 | 11/2008 | Kurrek |
| 2009/0042158 A1 | 2/2009 | Steiner |
| 2009/0274996 A1 | 11/2009 | Miller |
| 2009/0292288 A1 | 11/2009 | Hung |
| 2009/0326440 A1 | 12/2009 | Lee |
| 2010/0221681 A1 | 9/2010 | Hochman |
| 2010/0291511 A1 | 11/2010 | Lee |
| 2010/0324561 A1 | 12/2010 | Watzek |

OTHER PUBLICATIONS

Muronoi M, Xu H, Shimizu Y, and Ooya K., "Simplified procedure for augmentation of the sinus floor using a haemostatic nasal balloon," British Journal of Oral & Maxillofacial Surgery 41(2):120-121, 2003.

Summers, Robert B, DMD, "A New Concept in Maxillary Implant Surgery: The Osteotome Technique"; Compend. Contin. Educ. Dent., vol. XV, No. 2; 1994; 6 pages.

Summers, Robert B, DMD, "The Osteotome Technique: Part 2—The Ridge Expansion Osteotomy (REO) Procedure"; Compend. Contin. Educ. Dent., vol. XV, No. 24 1994; 7 pages.

Hernandez-Alfaro F, Torradeflot MM, Marti C. Prevalence and management of Schneiderian membrane perforations during sinus-lift procedures. Clin. Oral Impl. Res. 19, 2008; 91-98 doi: 10.1111/j.1600-0501.2007.01372.x 8 pages.

Javier Rambla Ferrer, Miguel Peñarrocha Diago, Juan Guarinos Carbó, "Analysis of the Use of Expansion Osteotomes for the Creation of Implant Beds . . . Technical Contributions and Review of the Literature," Med. oral patol. oral cir.bucal (Internet) v.11 n.3 Madrid May-Jun. 2006; 7 pages.

Laksman Dene; Ridge Expansion and Immediate Implant Placement in the Esthetic Zone; NYSDY; Mar. 2010; 4 pages.

* cited by examiner

VARIABLE GEOMETRY OSTEOTOME FOR RIDGE EXPANSION

CROSS REFERENCES TO RELATED APPLICATIONS

This application claims priority on U.S. Provisional Application 61/705,659, filed on Sep. 26, 2012; and is a continuation-in-part of U.S. application Ser. No. 13/942,920, filed on Jul. 16, 2013, which claims priority on U.S. Provisional Application Ser. No. 61/674,121, filed on Jul. 20, 2012; and is a continuation-in-part of U.S. application Ser. No. 14/033,031, filed on Sep. 20, 2013, which claims priority on U.S. Provisional Application Ser. No. 61/703,838, titled "Multi-Functional Osteotome and Method of Use for Sinus Lift Procedure," filed on Sep. 21, 2012, and claims priority on U.S. Provisional Application Ser. No. 61/714,345, filed on Oct. 16, 2012. The disclosures of each these applications are incorporated herein by reference.

FIELD OF THE INVENTION

The present invention relates to improvements in the Osteotomes used in the crestal approach for the sinus lift procedure, and more particularly to a series of Osteotome tips that cause less stress and a correspondingly reduced tendency toward fracturing of the crestal area.

BACKGROUND OF THE INVENTION

There are many conditions which may result in a person becoming partially or completely edentulous (periodontal disease, an injury, etc.), which is commonly remedied today by dental implants. Dental implants are endosseous, being a "root" device that is usually made of titanium, where the implants are inserted into the jaw through the bone at the alveolar ridges, after which a healing period on the order of months is necessary for osseointegration. During this healing period the bone will grow in and around the implant to provide support.

The alveolar ridges are columns of bone, found on both the maxilla and the mandible, that surround and anchor the teeth within sockets known as alveoli. However, the alveolar bone quickly becomes atrophic in the absence of teeth, typically resulting in lack of sufficient bone mass for successful implantation. In the Maxilla, when sinus pneumatization decreases available bone after tooth loss, a sinus elevation procedure prior to implant placement is required to increase the amount of bone therein. The sinus lift procedure may be performed either through a lateral approach or a crestal approach.

In the crestal approach for a sinus lift procedure of the posterior maxilla (upper jaw), to which the improvements of the present invention is directed, a pilot drill may initially be used to create a small hole in the crestal cortex to reach the cancellous layer, and to form an implant insertion axis. The anatomical characteristics of the posterior maxilla, particularly the existence of its more spongy (cancellous) bone, enable it to successfully lend itself to undergo the ridge expansion osteotomy technique developed by R. B. Summers (see e.g., Summers, DMD, Robert B, "A New Concept in Maxillary Implant Surgery: The Osteotome Technique;" 1994; Summers, DMD, Robert B, "The Osteotome Technique: Part 2—The Ridge Expansion Osteotomy (REO) Procedure;" 1994; and Summers, DMD, Robert B, "The Osteotome Technique: Part 3-Less Invasive Methods of Elevating the Sinus Floor;" 1994).

The technique causes expansion of the pilot hole without further elimination of bone material, and generally compresses the bone and increases bone density, in the surgeon's favor. The technique uses a succession of conical expansion Osteotome tools having a gradual diameter escalation. The smallest caliber expansion Osteotome tool is inserted manually into the pilot hole, with pressing and rotating of the tool occurring until the desired depth is reached, or until further penetration is resisted, at which time gentle tapping using a surgical mallet on the Osteotome may cause it to reach the proper depth. Further use of successively larger Osteotome tools causes lateral compression that increases bone density and the size of the opening. The procedure is typically carried out by an oral surgeon using different calibers of Osteotomes that are constructed such that the initial diameter of a successively larger Osteotome is the same as the largest penetrating diameter of the previous conical Osteotome that was used, thereby providing a constant progression of increasing separation.

The procedure exhibits high success rates if the sinus membrane was not breached during the procedure, as discussed in the by Hernandez-Alfaro F, Torradeflot MM, and Marti C., title "Prevalence and Management of Schneiderian Membrane Perforations during Sinus-lift Procedures." But a further consideration for the success of the implant concerns the impact of the Summers' diameter escalation on the crest of the alveolar ridge, when the ridge has undergone resorption producing a knife-edged shape, rather than its tall, rounded shape. The present invention offers various improvements to aid the oral surgeon, including Osteotome configurations and a method of use that reduce fracturing of the crest of the alveolar ridges—the most vulnerable area of the ridge during the osteotomy.

OBJECTS OF THE INVENTION

It is an object of the invention to provide a series of Osteotomes that are constructed to perform a ridge expansion osteotomy.

It is another object of the invention to provide a series of ridge expansion Osteotomes that are particularly adapted to reduce stress on the crestal cortex to reduce the possibility of fracture.

It is a further object of the invention to provide a series of ridge expansion Osteotomes that are particularly adapted to cause more expansion apically and less expansion crestally while proceeding deeper into the osteotomy to working depth.

It is another object of the invention to provide a mathematical formula for the definition of the Osteotome diameter escalation that serves to reduce/eliminate excessive stress at the crestal cortex.

Further objects and advantages of the invention will become apparent from the following description and claims, and from the accompanying drawings.

SUMMARY OF THE INVENTION

The Osteotomes commonly used for a ridge expansion osteotomy include tips that follow the escalation that was prescribed by Robert Summers, DMD, as documented in his articles that were noted above. This prescribed diameter escalation is such that the initial diameter of a successively larger Osteotome instrument is the same as the largest penetrating diameter of the conical tip of the previous Osteotome that was used. This conventional diameter escalation is suitable for the osteotomy on a patient where there has not been any significant local bone resorption at the implant site, and the alveolar ridge remains tall, and possesses a rounded crest. However, where bone resorption has progressed so as to noticeably reduce the height of the ridge locally and produce a knife-edged shape, this traditional osteotome diameter escalation will tend to result in excessive stress within the reduced bone mass at the pointed crest, with the increased possibility of fracturing off a piece of bone at that location, which is crucial for successfully implanting a platform.

The Osteotomes of the present invention have been developed to address this problem with the prior art. The tips of the Osteotomes of the present invention are also conical, but utilize a diameter escalation that may not be in accord with the escalation prescribed by Summers (the initial diameter of a successively larger Osteotome instrument is the same as the largest penetrating diameter of the conical tip of the previously used Osteotome), and may furthermore use a different scheme for escalation of the diameters at the apex of the tips, than for the escalation of the diameters at the base of the tips.

The scheme for escalating the apex of the conical tips of successive Osteotomes, consists of a linear incremental increase in the diameters thereat. The scheme for escalating the base of the conical tips of successive Osteotomes, consists of a step-wise increase in those diameters, so that only every other incremental increase in the diameter of the tip is accompanied by an increase in the diameter at the base of the cone shape. This assures that a requisite amount of work towards compaction and expansion of the bone at a position slightly below the crest, has been accomplished prior to such compaction at the crest itself, to decrease the possibility of a fracture. Other mathematical relationships also exist with regard to the apex and base of the tips at respective stages of those incremental increases, which are discussed further hereinafter.

DETAILED DESCRIPTION OF THE INVENTION

Figure 1:
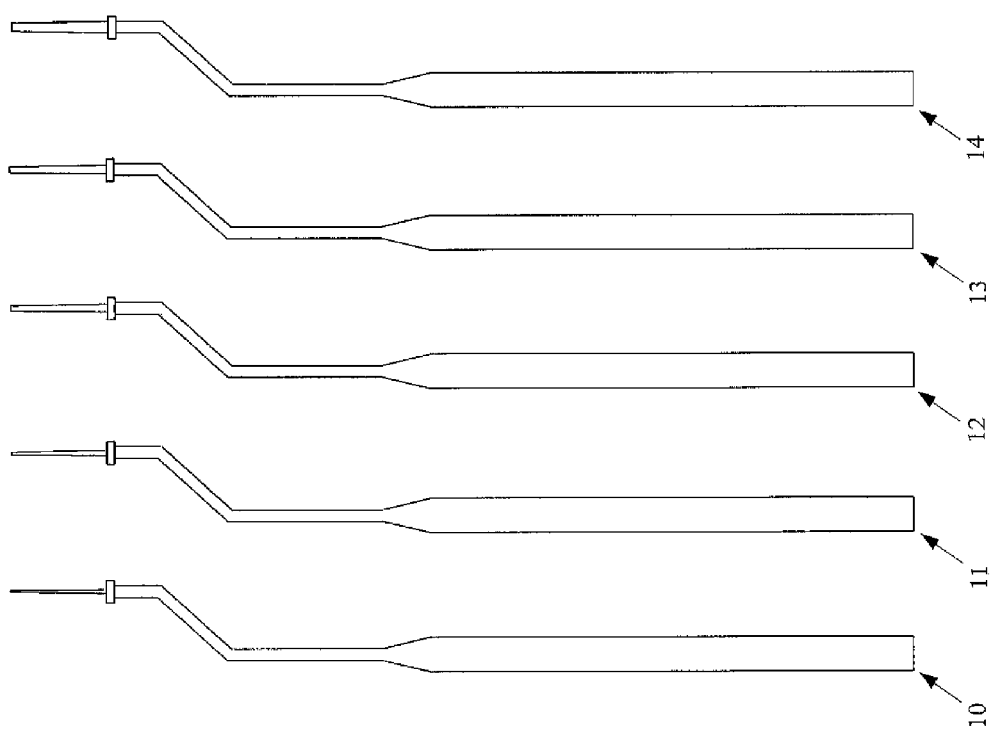
FIG. 1 illustrates a series of Osteotomes of the prior art, which exhibit conventional escalation of the conical diameters for successive Osteotomes.
Figure 2:
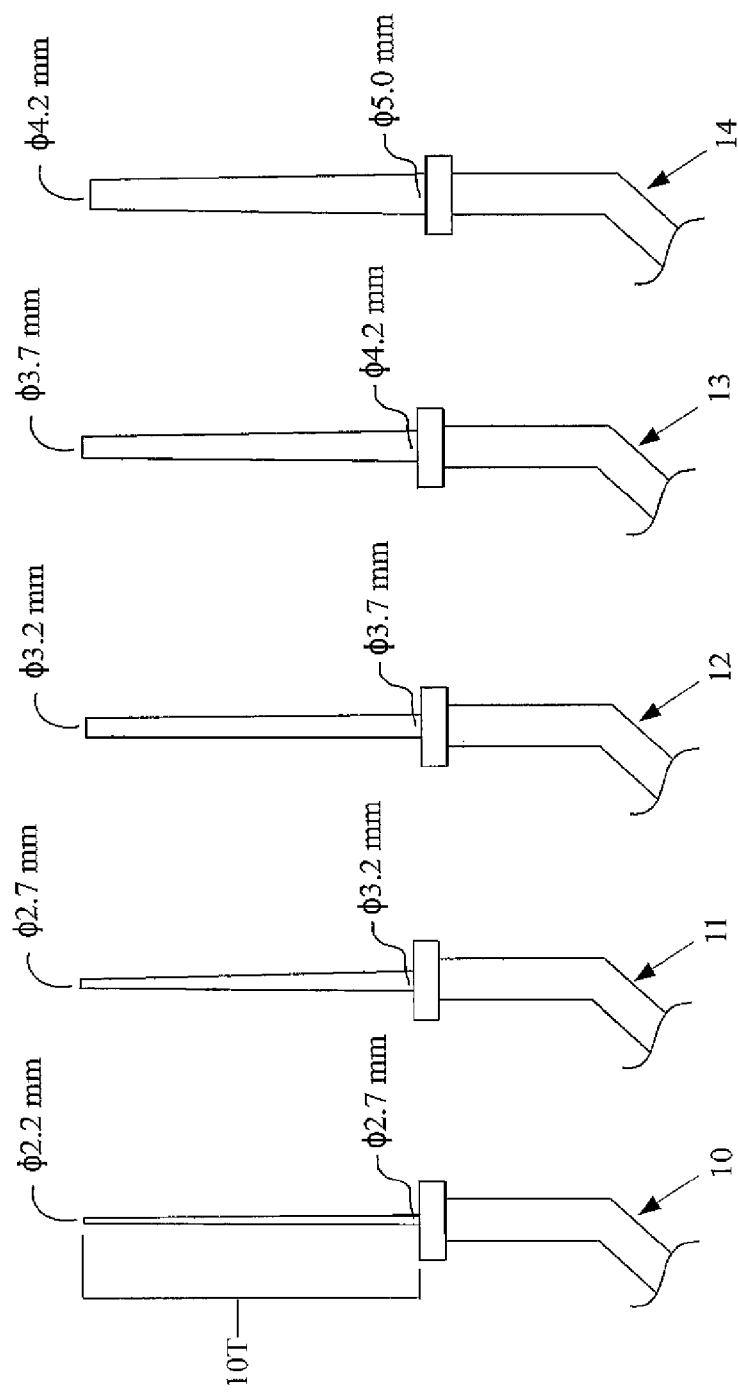
FIG. 2 is an enlarged detail view of the tips of the Osteotomes of FIG. 1, illustrating the Summers' diameter escalation, whereby the initial diameter of a successively larger Osteotome is the same as the largest penetrating diameter of the previous conical Osteotome that was used.

FIG. 1 shows a series of prior art Osteotomes that are usable for providing the necessary expansion and compaction of bone surrounding an implant pilot hole formed in an alveolar ridge during a sinus lift procedure. The tips for each of the Osteotomes, shown enlarged within FIG. 2, may be tapered so as to be formed with a conical shape, as seen for tip 10T of Osteotome 10. The base of the conical tip may have a first diametrical value, and the free end of the tip may have a second diametrical value, being less that the diametrical value of the base. A typical set of expansion Osteotomes usable for the sinus lift procedure may thus include, for example, a handle with a tip tapering from 2.2 mm to 2.7 mm, another handle with a tip tapering from 2.7 mm to 3.2 mm, a handle with a tip tapering from 3.2 min to 3.7 mm, a handle with a tip tapering from 3.7 mm to 4.2 mm, and a handle with a tip tapering from 4.2 mm to 5.0 mm.

It may thus be seen that typical Summers' expansion Osteotome instruments have been constructed "with gradual diameter escalation from one instrument to the next, whereby the base of each instrument corresponded to the active portion of the next instrument . . . ," as recounted by Javier Rambla Ferrer, Miguel Peñarrocha Diago, Juan Guarinos Carbó, in the paper titled, "Analysis of the Use of Expansion Osteotomes for the Creation of Implant Beds . . . Technical Contributions and Review of the Literature."

Figure 3B:
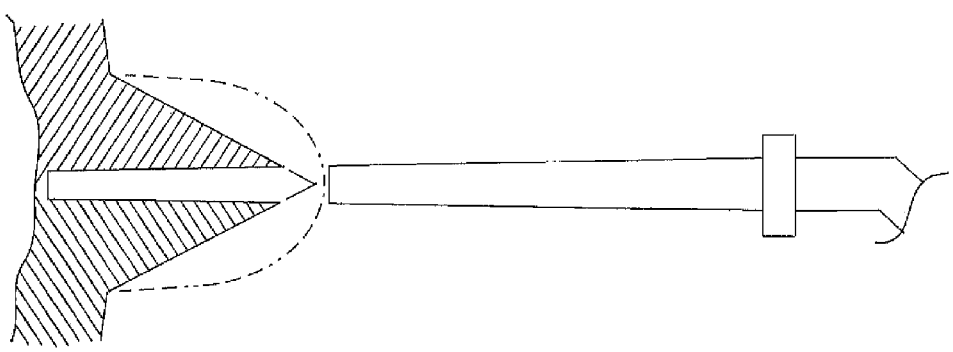
FIG. 3B illustrates a cross-section through an alveolar ridge, showing an alveolar ridge that has undergone resorption, resulting in a shallower and pointed crest.
Figure 3A:
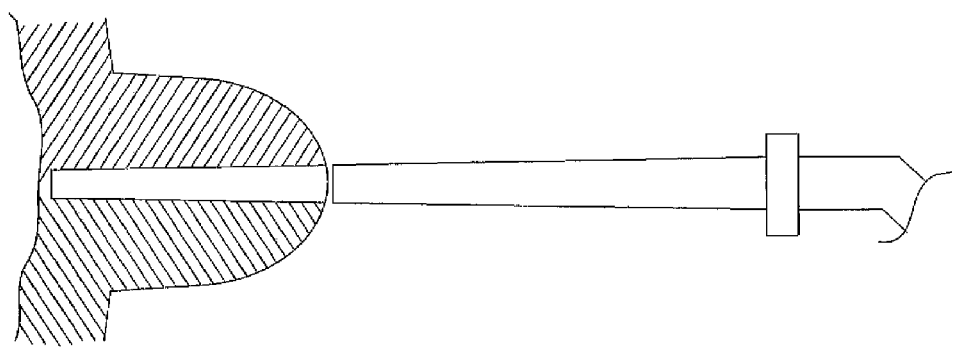
FIG. 3A illustrates a cross-section through an alveolar ridge, showing a tall rounded crest that has not been subjected to resorption.

This typical Summers' diameter escalation has shown good success, generally speaking, but suffers a serious drawback for many dental implant patients. The progression for bone resorption following loss of a tooth is rapid. The alveolar ridge changes from a high well-rounded ridge, as seen in FIG. 3A, to a knife-edged ridge shape, as seen in FIG. 3B. The resorption results in loss in the width at the crest. Although use of the typical diameter escalation is acceptable in the case where no significant resorption has occurred, because there is still sufficient bone mass at the crestal region to support the forces imposed by insertion of the larger diameter of the successive instruments, the same is not true after resorption has progressed. Where bone resorption has caused the ridge to be lowered and to develop a sharp edge, there often is insufficient bone mass at the crestal portion to support the expansion forces and the ridge bone would tend to pivot closer to the crest, which may result in the fracturing off of precious bone material, further reducing the height of the ridge.

Figure 4:
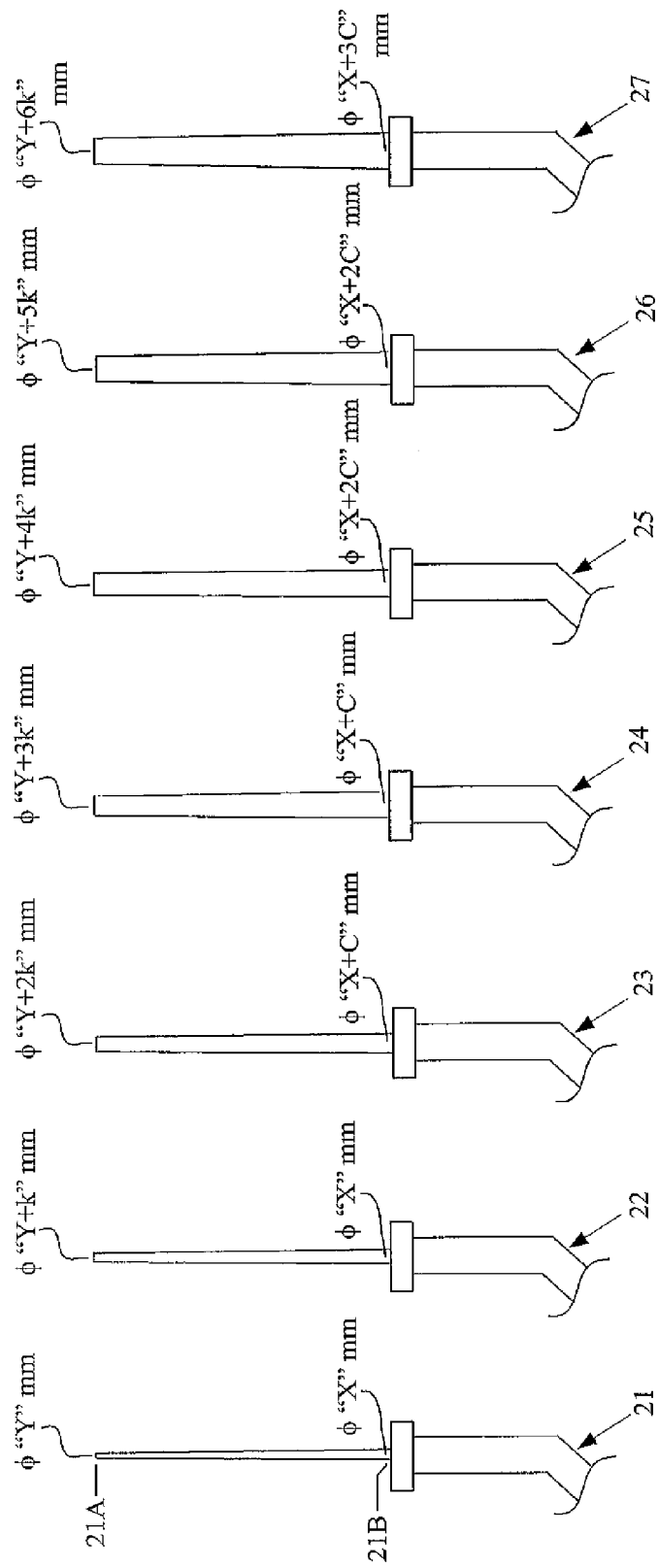
FIG. 4 illustrates the series of Osteotome tips of the current invention that are constructed in accordance with a diameter escalation specific for the base and for the free end of the tip, to ensure reduced crestal alveolar stress during the osteotomy.

FIG. 4 shows a series of Osteotome tips of the present invention that may be constructed to have a unique diameter escalation that is different for the base of the tip than for the free end of the tip, and which is susceptible to definition by a mathematical formula. This unique escalation creates an improved Osteotome tip that is better adapted to providing less stress to the crestal region for the patient where bone resorption is a considerable factor. The progression for size increases in the diameter of the conical tip at its apex (free end) occurs in a linear fashion, while the progression for size increases in the diameter of the conical tip at its working base occurs as a step function (also termed a "stair" function).

The diameter of the conical tip for the first instrument 21 at its free end—apex 21A, may have an initial value "Y" that may be, for example, the 2.2 mm diameter of the above-mentioned Osteotome set. Thereafter, the initial diameter "Y" of the conical tip at the apex 21A of the first instrument 21 may be incrementally increased by a value "k" to create the diameter ($\phi=Y+k$) at the apex 22A of the second instrument 22. The diameters at the apex of the third, fourth, and fifth instruments (23, 24, 25), etc., may thereafter be similarly incremented, with those diameters being, Y+2k, Y+3k, Y+4k, etc.

The diameter of the conical tip for the first instrument 21 at its base 21B may have an initial value "X" that may be, for example, the 2.7 mm diameter of the above-mentioned Osteotome set. Thereafter, the initial diameter "X" of the conical tip at its base 21B of the first instrument 21 may remain unchanged and still be the value "X" for the base 22B of the second instrument 22, forming the level portion of the first "step." Next, the diameter "X" of the conical tip at its base 23B of the third instrument 23 may be the "stair riser" as it may be incrementally increased above the diametrical value of the base 22B of the second instrument 22 by a value "C" to create the diameter=X+C. The diameter at the base of the fifth and seventh instruments (25, 27), etc., may also be the "stair riser" and may be similarly incremented, with those diameters being, X+2C, X+3C, etc., while the diameters at the base of the fourth and sixth instruments (24, 26), etc., may be the "stair step" and may not be incrementally changed.

To be useful in accordance with the Osteotome technique of the present invention, and while nonetheless being in accord with the Summers' technique, the diameter of the tip for the first instrument herein at its base must be larger than the value for the diameter of the tip at its apex, to form the conical shape (i.e., X>Y). It also follows that thereafter, X+C>Y+3k; and similarly, X+2C>Y+5k, and at least that X+3C>Y+6k, etc. The incremental value used for the increase of the diameter at the apex could be the same as the incremental value used for the increase of the diameter at the base (i.e., it may be that k=C). However, from a practical standpoint, to maintain the conical shape during escalation, whereby the tip possesses the smaller diameter, and to satisfy other requirements, the values will not be the same (i.e., k≠C).

In order to protect the knife-edged crest of the ridge, the osteotomes of the present invention may be constructed such that the diameter of the free end, $\phi_{FE}$, of the successive osteotome to be used (see FIG. 3C), is smaller than the diameter of the base, $\phi_b$, of the osteotome that was just previous utilized in the implant socket. This may be expressed mathematically, in that Y+k≤X (the appropriate conical relationship), and it must also be true that Y+2k≤X. Similarly, it also follows that: Y+4k≤X+C; and that: Y+6k≤X+2C. Note that in FIG. 3C, the working base of the tip may be identified on the Osteotome by a marking thereon, rather that utilizing a protruding rigid stop, as the stop could potentially impact the fragile ridge crest when the Osteotome is being driven by a mallet to the proper working depth. Also, depending upon the amount of difference between the diameter of the free end ($\phi_{FE}$) of the successive osteotome to be used and the diameter of the base ($\phi_b$) of the previous Osteotome, there may be some acceptable range in the depth of usage for particular Osteotomes.

Figure 3C:
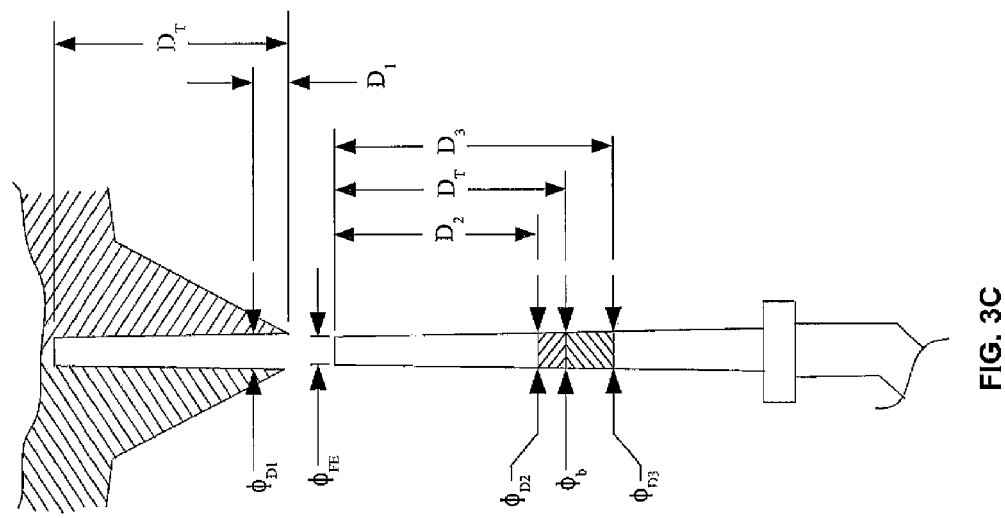
FIG. 3C is a cross-sectional view illustrating use of an Osteotome of the present invention on an implant socket of an alveolar ridge that has undergone significant resorption.

This is shown by the hatching in FIG. 3C, where $\phi_{D3}$ is the osteotome diameter at a greater depth ($D_3$) than a standard depth, $D_T$. Since $\phi_{D3}$ is larger than $\phi_b$ on that Osteotome, the constraint that the diameter of the free end ($\phi_{FE}$) of the successive osteotome to be used be smaller than the diameter of the working base ($\phi_b$) of the previously used osteotome will always be true for a greater depth socket (i.e., in this case, because of the depth of the socket is at depth $D_3$ instead of $D_T$, the effective base will be at $\phi_{D3}$); however, the effectiveness of the successive tools will be decreased substantially if the cross-hatched range for $\phi_{D3}$ is not limited, and would require a very large number of Osteotomes in the set to complete socket formation.

The reverse cross-hatched region between $\phi_b$ and $\phi_{D2}$ may also be indicated on the Osteotome, because it may show the extent to which a shallower depth socket may be accommodated, at which $\phi_{D2}$ becomes the effective base, and where this would nonetheless fulfill the requirement that the diameter of the free end ($\phi_{FE}$) of the next osteotome to be used will be smaller than $\phi_{D2}$ of the Osteotome of FIG. 3C.

In addition to the above cited requirements, the set of Osteotomes constructed according to the present invention may be even more effective at preventing damage to the crest of the ridge where the diameter of the free end of the successive osteotome ($\phi_{FE}$) preferably begins to engage the socket at a depth $D_1$ (i.e., $\phi_{FE}=\phi_{D1}$). The engagement depth $D_1$ may preferably be at least 5% of the total depth $D_T$, and may preferably not be more that 40% of the total depth $D_T$. It is more preferable that the ratio of the engagement depth $D_1$ to the socket depth $D_T$ fall within the following range:

$$0.1 \leq D_1/D_T \leq 0.25.$$

If engagement were to occur at a depth of less than 5% of the total depth (i.e., close to the sharp crest of the ridge), excess stress will be introduced at that location, risking failure (fracturing) due to the greater strength of the ridge immediately below. Also, if the engagement depth were to occur at a substantial portion of the total depth, very little work towards compaction of the socket would occur for each osteotome, which would again necessitate the use of numerous Osteotomes in the set to complete the process.

The equation to describe the linear increase in the diameter at the apex for each of the Osteotome instruments may be given by the equation:

$$\phi_{An} = Y + (n-1)(k)$$

where n is the numbered Osteotome instrument in the set, and may range from the first Osteotome instrument to be used (i.e., n=1) to the last Osteotome instrument in the set (i.e., where there are seven Osteotome instruments in the set, for the seventh, n=7).

The equation to describe the step-wise increase in the diameter at the base for each of the Osteotome instruments is related to the step equation for f, where:

$$f(x) = \sum_{i=0}^{n} \alpha_i \chi_{A_i}(x) \text{ for all real numbers } x$$

where n≥0, $\alpha_i$ are real numbers, $A_i$ are intervals, and $\chi_A$ is the indicator function of A. (see e.g., Bachman, Narici, Beckenstein, "Example 7.2.2", Fourier and Wavelet Analysis. Springer, New York, 2000; and http://en.wikipedia.org/wiki/Step_function, with the disclosures of each being incorporated herein by reference). The difference with the step function as utilized herein is that each step for the incremental increase in the diameter of the base of the tip occurs only for every other Osteotome instrument, rather than for each instrument.

Construction of the tip of the set of Osteotome instruments in accordance with this linear function for the increasing diameter at the apex and the step function for the increasing diameter at the base of the tips, and the disclosed restriction, serves to reduce the stress on the crestal portion of the alveolar ridges during the osteotomy. This reduced stress will often help preserve critical bone mass at the crest of the ridge, and help improve the implant survival rate, by reducing or eliminating the tendency towards fracturing a portion of the crest.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

I claim:

1. A number of osteotomes, n, forming a set of osteotomes, for use during a ridge expansion osteotomy to reduce crestal alveolar stress and to reduce likelihood of a crestal fracture, each said osteotome of said set comprising a conical working tip with a free end having a diameter $\phi_{An}$, and a working base; a first osteotome, n=1, of said set comprising said working tip formed with a first diameter, $\phi_{A1}$=Y, at said free end, and with a second diameter, X, at said working base, said second diameter being larger than said first diameter, X>Y; and wherein for each successive osteotome of said set, said diameter at said free end increases linearly by a constant increment, k, and said diameter at said working base alternately increases by a constant increment, C, as a step function.

2. The set of osteotomes according to claim 1, wherein said diameter, $\phi_{An}$, at said free end of each of said set of n osteotomes is defined by:

$$\phi_{An} = Y + (n-1)(k).$$

3. The set of osteotomes according to claim 2, wherein n=4 and said set of osteotomes comprises four osteotomes;
   wherein said free end for said second osteotome has a diameter of Y+k;
   wherein said free end for said third osteotome has a diameter of Y+2k;
   wherein said free end for said fourth osteotome has a diameter of Y+3k;
   wherein said working base for said second osteotome has a diameter of X;
   wherein said working base for said third osteotome has a diameter of X+C;
   wherein Y+2k≤X; and
   wherein X+C>Y+3k.

4. The set of osteotomes according to claim 3, wherein k≠C.

5. The set of osteotomes according to claim 4, wherein n=7 and said set of osteotomes comprises a total of seven osteotomes;
   wherein said free end for said fourth osteotome has a diameter of Y+3k;
   wherein said free end for said fifth osteotome has a diameter of Y+4k;
   wherein said free end for said sixth osteotome has a diameter of Y+5k;
   wherein said free end for said seventh osteotome has a diameter of Y+6k;
   wherein said working base for said fourth osteotome has a diameter of X+C;
   wherein said working base for said fifth osteotome has a diameter of X+2C;
   wherein said working base for said sixth osteotome has a diameter of X+2C;
   wherein said working base for said seventh osteotome has a diameter of X+3C;
   wherein Y+4k≤X+C;
   wherein Y+6k≤X+2C;
   wherein X+C>Y+3k;
   wherein X+2C>Y+5k; and
   wherein X+3C>Y+6k.

* * * * *